(12) United States Patent
Riggs-Sauthier et al.

(10) Patent No.: US 8,754,197 B2
(45) Date of Patent: Jun. 17, 2014

(54) SYNTHESIS OF AZO BONDED IMMUNOREGULATORY COMPOUNDS

(71) Applicants: Jennifer A. Riggs-Sauthier, Huntsville, AL (US); Nnochiri N. Ekwuribe, Cary, NC (US)

(72) Inventors: Jennifer A. Riggs-Sauthier, Huntsville, AL (US); Nnochiri N. Ekwuribe, Cary, NC (US)

(73) Assignee: Biocon Limited (IN)

( * ) Notice: Subject to any disclaimer, the term of this patent is extended or adjusted under 35 U.S.C. 154(b) by 0 days.

(21) Appl. No.: 13/680,434

(22) Filed: Nov. 19, 2012

(65) Prior Publication Data
US 2013/0096286 A1    Apr. 18, 2013

Related U.S. Application Data

(62) Division of application No. 13/094,135, filed on Apr. 26, 2011, now Pat. No. 8,314,214, which is a division of application No. 11/631,582, filed as application No. PCT/US2005/024109 on Jul. 7, 2005, now Pat. No. 7,932,366.

(60) Provisional application No. 60/585,995, filed on Jul. 7, 2004.

(51) Int. Cl.
*C07C 245/08* (2006.01)

(52) U.S. Cl.
USPC ........................................ 534/585

(58) Field of Classification Search
None
See application file for complete search history.

(56) References Cited

U.S. PATENT DOCUMENTS

| | | |
|---|---|---|
| 297,852 A | 4/1884 | Roussin et al. |
| 406,670 A | 7/1889 | Sandmeyer |
| 1,157,169 A | 10/1915 | Mettler |
| 2,270,676 A | 1/1942 | Behnisch et al. |
| 2,314,023 A | 3/1943 | Straub et al. |
| 2,336,275 A | 12/1943 | McNally et al. |
| 2,344,244 A | 3/1944 | Freed et al. |
| 2,396,019 A | 3/1946 | Murray |
| 2,551,003 A | 5/1951 | Johnson, Jr. |
| 3,244,694 A | 4/1966 | May et al. |
| 3,345,356 A | 10/1967 | Kmiecik |
| 3,641,040 A | 2/1972 | Carney et al. |
| 3,669,956 A | 6/1972 | Borck et al. |
| 3,915,951 A | 10/1975 | Agback et al. |
| 4,189,607 A | 2/1980 | Amano et al. |
| 4,298,595 A | 11/1981 | Parkinson et al. |
| 4,348,399 A | 9/1982 | Shepherd |
| 4,374,932 A | 2/1983 | Pitzele et al. |
| 4,412,992 A | 11/1983 | Chan |
| 4,455,305 A | 6/1984 | Rokos |
| 4,472,433 A | 9/1984 | Ueda et al. |
| 4,493,823 A | 1/1985 | Moller et al. |
| 4,496,553 A | 1/1985 | Halskov |
| 4,504,494 A | 3/1985 | Grollier et al. |
| 4,528,367 A | 7/1985 | Agback et al. |
| 4,539,198 A | 9/1985 | Powell et al. |
| 4,540,685 A | 9/1985 | Bauer |
| 4,559,330 A | 12/1985 | Agback et al. |
| 4,591,584 A | 5/1986 | Agback |
| 4,595,699 A | 6/1986 | Terada et al. |
| 4,628,083 A | 12/1986 | Agback |
| 4,632,921 A | 12/1986 | Bauer |
| 4,657,900 A | 4/1987 | Powell et al. |
| 4,663,308 A | 5/1987 | Saffran et al. |
| 4,664,256 A | 5/1987 | Halskov |
| 4,670,112 A | 6/1987 | Lund |

(Continued)

FOREIGN PATENT DOCUMENTS

| | | |
|---|---|---|
| DE | 4121849 A1 | 1/1993 |
| EP | 0094599 A1 | 11/1983 |

(Continued)

OTHER PUBLICATIONS

Effenberger et al. Tetrahedron Asymmetry 12, 2001 279-285.*

(Continued)

*Primary Examiner* — Brandon Fetterolf
*Assistant Examiner* — Ana Z Muresan
(74) *Attorney, Agent, or Firm* — Marianne Fuierer; Moore & Van Allen, PLLC

(57) ABSTRACT

Methods are disclosed for preparing compounds of Formula I:

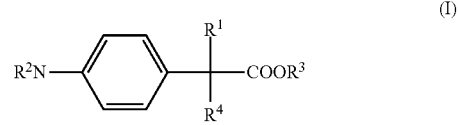

where $R^1$, $R^3$, and $R^4$ are independently hydrogen or $C_1$ to $C_4$ alkyl, and $R^2$ is:

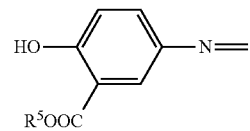

where $R^5$ is selected from the group consisting of hydrogen and $C_1$ to $C_4$ alkyl, or

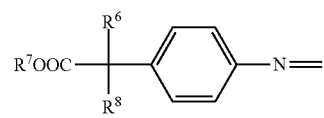

where $R^6$, $R^7$ and $R^8$ are independently hydrogen or $C_1$ to $C_4$ alkyl; or the esters or pharmacologically acceptable salts thereof. The compounds and or their metabolites can be used to treat or prevent various diseases, particularly inflammatory conditions of the GI tract.

8 Claims, 2 Drawing Sheets

(56) References Cited

U.S. PATENT DOCUMENTS

| | | |
|---|---|---|
| 4,699,902 A | 10/1987 | Bauer |
| 4,720,506 A | 1/1988 | Munakata et al. |
| 4,725,676 A | 2/1988 | Agback et al. |
| 4,737,240 A | 4/1988 | Davis et al. |
| 4,780,318 A | 10/1988 | Appelgren et al. |
| 4,788,331 A | 11/1988 | Sjöstrand |
| 4,837,229 A | 6/1989 | Rokos et al. |
| 4,849,416 A | 7/1989 | Pendleton et al. |
| 4,873,321 A | 10/1989 | Omura et al. |
| 4,880,794 A | 11/1989 | Halskov |
| 4,889,846 A | 12/1989 | Crossley |
| 4,904,765 A | 2/1990 | Derber et al. |
| 4,911,922 A | 3/1990 | Masuhara et al. |
| 4,920,206 A | 4/1990 | Behringer et al. |
| RE33,239 E | 6/1990 | Halskov |
| 4,933,330 A | 6/1990 | Jorgensen et al. |
| 4,960,765 A | 10/1990 | Halskov |
| 4,999,347 A | 3/1991 | Sorenson |
| 5,010,069 A | 4/1991 | Bottom et al. |
| 5,013,727 A | 5/1991 | Halskov |
| 5,026,560 A | 6/1991 | Makino et al. |
| 5,037,968 A | 8/1991 | Simon et al. |
| 5,041,431 A | 8/1991 | Halskov |
| 5,082,651 A | 1/1992 | Healey et al. |
| 5,089,468 A | 2/1992 | Yoshida et al. |
| 5,137,916 A | 8/1992 | Ulrich et al. |
| 5,244,922 A | 9/1993 | Burzynski |
| 5,254,587 A | 10/1993 | Burzynski |
| 5,272,176 A | 12/1993 | Ulrich et al. |
| 5,274,002 A | 12/1993 | Hawkins |
| 5,330,981 A | 7/1994 | Rosini et al. |
| 5,352,681 A | 10/1994 | Wittebrood et al. |
| 5,378,470 A | 1/1995 | Lahr |
| 5,391,575 A | 2/1995 | Burzynski |
| 5,393,779 A | 2/1995 | Holloway et al. |
| 5,409,711 A | 4/1995 | Mapelli et al. |
| 5,434,184 A | 7/1995 | Holloway et al. |
| 5,476,849 A | 12/1995 | Ulrich et al. |
| 5,480,910 A | 1/1996 | Holloway et al. |
| 5,484,605 A | 1/1996 | Scheiffele et al. |
| 5,487,770 A | 1/1996 | Dyllick-Brenzinger et al. |
| 5,498,608 A | 3/1996 | Johnson et al. |
| 5,502,078 A | 3/1996 | Holloway et al. |
| 5,514,676 A | 5/1996 | Ulrich et al. |
| 5,519,014 A | 5/1996 | Borody |
| 5,541,170 A | 7/1996 | Rhodes et al. |
| 5,541,171 A | 7/1996 | Rhodes et al. |
| 5,574,050 A | 11/1996 | Carrell et al. |
| 5,593,971 A | 1/1997 | Tschollar et al. |
| 5,602,183 A | 2/1997 | Martin et al. |
| 5,629,012 A | 5/1997 | Halskov |
| 5,629,020 A | 5/1997 | Leone-Bay et al. |
| 5,631,294 A | 5/1997 | Kurtz et al. |
| 5,635,533 A | 6/1997 | Samid |
| 5,637,618 A | 6/1997 | Kurtz et al. |
| 5,646,182 A | 7/1997 | Burzynski |
| 5,648,380 A | 7/1997 | Martin |
| 5,654,333 A | 8/1997 | Samid |
| 5,661,179 A | 8/1997 | Samid |
| 5,663,208 A | 9/1997 | Martin |
| 5,667,789 A | 9/1997 | Collin et al. |
| 5,668,123 A | 9/1997 | Berry |
| 5,674,912 A | 10/1997 | Martin |
| 5,696,243 A | 12/1997 | Beckmann et al. |
| 5,703,073 A | 12/1997 | Garvey et al. |
| 5,708,025 A | 1/1998 | Samid |
| 5,716,648 A | 2/1998 | Halskov et al. |
| 5,725,872 A | 3/1998 | Stamm et al. |
| 5,731,302 A | 3/1998 | Farolfi et al. |
| 5,739,299 A | 4/1998 | Hall |
| 5,747,477 A | 5/1998 | Carceller et al. |
| 5,747,532 A | 5/1998 | Lai |
| 5,770,708 A | 6/1998 | Bermes |
| 5,817,321 A | 10/1998 | Alakhov et al. |
| 5,827,332 A | 10/1998 | Zeidler et al. |
| 5,840,724 A | 11/1998 | Fenton et al. |
| 5,840,966 A | 11/1998 | Kumarathasan et al. |
| 5,843,994 A | 12/1998 | Samid |
| 5,852,056 A | 12/1998 | Samid |
| 5,861,426 A | 1/1999 | Del Soldato et al. |
| 5,866,608 A | 2/1999 | Kurtz et al. |
| 5,874,479 A | 2/1999 | Martin |
| 5,877,213 A | 3/1999 | Samid |
| 5,883,124 A | 3/1999 | Samid |
| 5,905,073 A | 5/1999 | Johnson et al. |
| 5,935,601 A | 8/1999 | Leone-Bay et al. |
| 5,939,455 A | 8/1999 | Rephaeli |
| 5,939,456 A | 8/1999 | Perrine |
| 5,945,411 A | 8/1999 | Larson et al. |
| 5,955,472 A | 9/1999 | Hays et al. |
| 5,962,710 A | 10/1999 | Gschneidner et al. |
| 5,973,126 A | 10/1999 | Ueno et al. |
| 5,985,927 A | 11/1999 | Kreutz |
| 6,008,208 A | 12/1999 | Petrie et al. |
| 6,008,250 A | 12/1999 | Kurtz et al. |
| 6,037,376 A | 3/2000 | Samid |
| 6,043,233 A | 3/2000 | Garvey et al. |
| 6,124,504 A | 9/2000 | Hupperts et al. |
| 6,127,349 A | 10/2000 | Chasalow |
| 6,183,549 B1 | 2/2001 | Wight |
| 6,191,265 B1 | 2/2001 | Hamprecht |
| 6,197,341 B1 | 3/2001 | Friess et al. |
| 6,225,296 B1 | 5/2001 | Kapadia |
| 6,245,735 B1 | 6/2001 | Pier |
| 6,245,802 B1 | 6/2001 | Iyengar et al. |
| 6,277,412 B1 | 8/2001 | Otterbeck |
| 6,277,836 B1 | 8/2001 | Borody |
| 6,281,203 B1 | 8/2001 | Touzan et al. |
| 6,294,186 B1 | 9/2001 | Beerse et al. |
| 6,313,107 B1 | 11/2001 | Vasudevan et al. |
| 6,319,951 B1 | 11/2001 | Chege |
| 6,326,364 B1 | 12/2001 | Lin et al. |
| 6,344,561 B2 | 2/2002 | Vuligonda |
| 6,348,497 B1 | 2/2002 | Billingham |
| 6,369,261 B1 | 4/2002 | Johnson et al. |
| 6,375,733 B1 | 4/2002 | Bindra |
| 6,380,256 B1 | 4/2002 | Vasudevan et al. |
| 6,383,471 B1 | 5/2002 | Chen et al. |
| 6,384,023 B2 | 5/2002 | Singleton et al. |
| 6,387,892 B1 | 5/2002 | Vasudevan et al. |
| 6,387,952 B1 | 5/2002 | Mazurek et al. |
| 6,391,832 B2 | 5/2002 | Lyons et al. |
| 6,399,647 B2 | 6/2002 | Kalgutkar et al. |
| 6,403,646 B1 | 6/2002 | Perimutter et al. |
| 6,409,812 B1 | 6/2002 | Ueno et al. |
| 6,413,494 B1 | 7/2002 | Lee et al. |
| 6,414,026 B1 | 7/2002 | Billingham |
| 6,423,696 B1 | 7/2002 | Collins et al. |
| 6,423,713 B1 | 7/2002 | Anantanarayan et al. |
| 6,426,338 B1 | 7/2002 | Borody |
| 6,437,104 B1 | 8/2002 | Nickel et al. |
| 6,444,221 B1 | 9/2002 | Shapiro |
| 6,458,776 B1 | 10/2002 | Ekwuribe et al. |
| 6,479,528 B1 | 11/2002 | Kuret et al. |
| 6,488,947 B1 | 12/2002 | Bekele |
| 6,495,552 B2 | 12/2002 | Vasudevan et al. |
| 6,528,076 B2 | 3/2003 | Small et al. |
| 6,541,670 B2 | 4/2003 | Ottosen |
| 6,551,620 B2 | 4/2003 | Otterbeck et al. |
| 6,551,632 B2 | 4/2003 | Borody |
| 6,552,077 B2 | 4/2003 | Cohen |
| 6,566,507 B2 | 5/2003 | Wood et al. |
| 6,573,252 B1 | 6/2003 | Del Soldato |
| 6,583,128 B2 | 6/2003 | Ekwuribe et al. |
| 6,583,273 B1 | 6/2003 | Bacher et al. |
| 6,589,944 B1 | 7/2003 | Rahbar |
| 6,599,748 B1 | 7/2003 | Nakajima et al. |
| 6,602,987 B1 | 8/2003 | Wilchek et al. |
| 6,613,807 B2 | 9/2003 | Uhrich |
| 6,630,463 B2 | 10/2003 | Kikuchi et al. |
| 6,653,352 B2 | 11/2003 | Barr et al. |
| 6,660,283 B2 | 12/2003 | Breton et al. |
| 6,720,344 B2 | 4/2004 | Kerwin et al. |
| 6,727,235 B2 | 4/2004 | Kreutz |

(56) References Cited

U.S. PATENT DOCUMENTS

| | | | |
|---|---|---|---|
| 6,791,788 | B2 | 9/2004 | Gustafson et al. |
| 6,808,616 | B2 | 10/2004 | Sanchez-Cano |
| 6,809,087 | B2 | 10/2004 | Carceller et al. |
| 6,824,786 | B2 | 11/2004 | Yu et al. |
| 6,867,233 | B2 | 3/2005 | Roselle et al. |
| 6,881,553 | B2 | 4/2005 | Kabbash et al. |
| 6,884,808 | B2 | 4/2005 | Kikuchi et al. |
| 6,887,632 | B2 | 5/2005 | Saminathan et al. |
| 6,903,082 | B2 | 6/2005 | Ekwuribe et al. |
| 6,907,736 | B2 | 6/2005 | Ohnishi et al. |
| 6,919,325 | B2 | 7/2005 | Linz et al. |
| 6,943,192 | B2 | 9/2005 | Burzynski |
| 6,949,555 | B2 | 9/2005 | Guitard et al. |
| 7,022,333 | B2 | 4/2006 | Syverson et al. |
| 7,030,146 | B2 | 4/2006 | Baynes et al. |
| 7,053,071 | B2 | 5/2006 | Dawson et al. |
| 7,064,185 | B2 | 6/2006 | Lau |
| 7,151,095 | B2 | 12/2006 | Ekwuribe et al. |
| 7,189,518 | B2 | 3/2007 | Schönbeck et al. |
| 7,238,680 | B2 | 7/2007 | Rosen |
| 7,265,153 | B2 | 9/2007 | Faller et al. |
| 7,425,578 | B2 | 9/2008 | Ekwuribe et al. |
| 2001/0016586 | A1 | 8/2001 | Guitard |
| 2001/0044466 | A1 | 11/2001 | Burnzynski et al. |
| 2001/0046509 | A1 | 11/2001 | Breton et al. |
| 2001/0046979 | A1 | 11/2001 | Roselle et al. |
| 2002/0002203 | A1 | 1/2002 | Rahbar |
| 2002/0061339 | A1 | 5/2002 | Stogniew et al. |
| 2002/0120008 | A1 | 8/2002 | Benzer et al. |
| 2002/0143011 | A1 | 10/2002 | Warrellow |
| 2002/0160986 | A1 | 10/2002 | Vasudevan et al. |
| 2002/0183285 | A1 | 12/2002 | Vasudevan et al. |
| 2002/0198348 | A1 | 12/2002 | Saminathan et al. |
| 2003/0013746 | A1 | 1/2003 | Hudson et al. |
| 2003/0017995 | A1 | 1/2003 | Khalifah et al. |
| 2003/0018069 | A1 | 1/2003 | Faller et al. |
| 2003/0018077 | A1 | 1/2003 | Billingham et al. |
| 2003/0077308 | A1 | 4/2003 | Rosen |
| 2003/0088233 | A1 | 5/2003 | Melles |
| 2003/0098243 | A1 | 5/2003 | Sanchez-Cano et al. |
| 2003/0108496 | A1 | 6/2003 | Yu et al. |
| 2003/0119792 | A1 | 6/2003 | Roca |
| 2003/0125306 | A1 | 7/2003 | Lan Hargest et al. |
| 2003/0130300 | A1 | 7/2003 | Linz et al. |
| 2003/0133966 | A1 | 7/2003 | Syverson et al. |
| 2003/0144276 | A1 | 7/2003 | Kikuchi et al. |
| 2003/0152566 | A1 | 8/2003 | Schonbeck et al. |
| 2003/0162754 | A1 | 8/2003 | Ligon |
| 2003/0166621 | A1 | 9/2003 | Keutz |
| 2003/0171306 | A1 | 9/2003 | Davis et al. |
| 2003/0176401 | A1 | 9/2003 | Carceller et al. |
| 2003/0176506 | A1 | 9/2003 | Dawson et al. |
| 2003/0181492 | A1 | 9/2003 | Baynes et al. |
| 2003/0181618 | A1 | 9/2003 | Saminathan et al. |
| 2003/0191146 | A1 | 10/2003 | Kabbash et al. |
| 2003/0191186 | A1 | 10/2003 | Ekwuribe et al. |
| 2005/0090553 | A1 | 4/2005 | Shapiro |
| 2007/0060552 | A1 | 3/2007 | Ekwuribe et al. |

FOREIGN PATENT DOCUMENTS

| | | |
|---|---|---|
| EP | 0036636 B1 | 2/1984 |
| EP | 0465802 A1 | 1/1992 |
| ES | 8606254 A1 | 5/1985 |
| GB | 2203434 A | 10/1988 |
| WO | WO 94/00135 | 1/1994 |
| WO | WO 95/31194 | 11/1995 |
| WO | WO 02/018324 | 7/2002 |

OTHER PUBLICATIONS

Rosalind P. Chan et al. Studies of Two Novel Sulfasalazine Analogs, Ipsalazide and Balsalazide; Digestive Diseases and Sciences; Jul. 1983; vol. 28, No. 7; Digestive Disease Systems, Inc.

Paul Retgeerts; Strategies in the prevention of post-operative recurrence in Crohn's Disease; Best Practice & Research Clinical Gastroenterology; 2003; pp. 63-73; vol. 17, No. 1; Elsevier Science Ltd.

M.C. Di Paolo et al. Sulphasalazine and 5-aminosalicylic acid in long-term treatment of ulcerative colitis: report on tolerance and side-effects; Digest Liver Dis.; 2001; pp. 563-569; 33.

E. K. Fields et al. Diaryl Substituted Maleic Anhydrides; J. Org. Chem.; 1990; pp. 5165-6170; 55; American Chemical Society.

Friedrich Nerdel et al. Chemical Abstracts; 1961; pp. 443-444; vol. 55.

Beilstein Search Results, 5522653.

Frank D. King; Bioisosteres, Conformational Restriction, and Prodrugs—Case History: An Example of a Conformational Restriction Approach; Medicinal Chemistry : Principles and Practice; 1994; pp. 206-225 (pp. 216-217, Table 4); Cambridge, RSC, GB.

Brown, Joseph P (1983) A polymeric Drug for Treatment of Inflammatory Bowel Disease, Journal of Medicinal Chemistry, vol. 26, 9, 1300-1301.

Rubinstein Abraham, et al. "Biodegradable Polymeric Matrices with Potential Specificity to the Large Intestine"; Oral Colon-Specific Drug Delivery, Chapter 9; pp. 233-267; USA (1992).

Kopeček Jindřich, et al. "N-(2-Hydroxypropyl)Methacrylamide Copolymers for Colon-Specific Drug Delivery"; Oral Colon-Specific Drug Delivery, Chapter 7; pp. 189-211; USA (1992).

Nerdel, F., ""Chromoisomerism" of p-Nitrobenzyl Cyanide." Justus Liebigs Annalen der Chemie, 632, 55-65, 1960.

Srinivasam G.R. et al. "The Synthesis of Azo Compounds from Nitro Compounds Using Lead and Triethylammonium Formate", Tetrahedron Letters, 44(31), 5835-5837, 2003.

Wheeler, O.H. et al. "Oxidation of Primary Aromatic Amines with Manganese Dioxide", Tetrahedron Letters, 20(2), 189-193, 1964.

Ferro, Michelle et al. "Structure Determination of APAZA, a Small, Novel, Diazo Molecule Currently Being Developed for Treatment of Inflammatory Bowel Disease (IBD)", Chemical Abstracts, 2005:191575, 2005.

Juodaityte, Jovita et al. "Synthesis of Photoswitchable Amino Acids Based on Azobenzene Chromophores: Building with Potential for Photoresponsive Biomaterials", Journal of Biotechnology, 112, 127-138, 2004.

McVey, Douglas C. et al. "Inhibition of Clostridium Difficile Toxin A-Induced Colitis in Rats by AZPAZA", Digestive Diseases and Sciences, 50 (3), 565-573, Mar. 2005.

Abiraj, K. et al. "Transfer Hydrogeneration of Aromatic Nitro Compounds Using Polymer-Supported Formate and Pd—C", Synthetic Communications, 35, 223-230, 2005.

Osman, Peter et al. "Optical Modulationof the Insertion of Gramicidin into Bilayer Lipid Membranes", Langmuir, 14, 4238-4242, 1998.

English Translation of Nerdel, Frederick et al. "Chromoisomerism of p-Nitrobenzyl Cyanide", Justus Liebigs Annalen der Chemie, 632, 55-65, 1960.

Nerdeli, F., "Chromoisomerism of p-Nitrobenzyl cyanide." Chemical Abstracts, 55:2446, 1961.

Database Crossfire Beilstein Online; Beilstein Institut Zur Foerderung Der Chemischen Wissenschaften, Frankfurt, AM Main, De; Database-Accession No. 926638 (BRN), XP002192315 & Journal of Organic Chemistry, vol. 55, No. 17, 1990, pp. 5165-5170; Easton, US.

Tse-Tsing Chu et al. A Proof of the Unsymmetrical Structure of the Azoxy Group; Journal of the American Chemical Society; 1993; pp. 2841-2850; 55; USA.

Par E. Frommel et al. La paraminobenzolsulfonesuccinylimide, sulfamide soluble neutre et injectable; Holv. Physiol. Acta; 1945; pp. 261-268; 3.

E. Hackmann et al. Nuovi Azoderivati Solfammidici; Boll. Chim. Farm.; 1975; pp. 501-508; 114.

B.C. Jain et al.; Studies in Sulphanilamides. Part XIII Reaction with Dicarboxylic Acids. Some New $N^1$- and $N^4$-Acyl and Heterocyclic Derivatives; J. Indian Chem. Soc.; 1947; pp. 173-176; 24.

Isami Kimura et al. Determination of the Active Moiety of BX661A, a New Therapeutic Agent for Alcerative Colitis, by Studying Its Therapeutic Effects on Ulcerative Colitis Induced by Dextran Sulfate Sodium in Rats; Drug Res.; 1998; pp. 1091-1096; 48 (II) (11).

(56) References Cited

OTHER PUBLICATIONS

S. A. A. Osman et al. Synthesis of Sulfanilamido-Naphthoquinones as Potential Antituberculous Agents; Journal of Pharmaceutical Sciences; Jan. 1983; pp. 68-71; vol. 72, No. 1; American Pharmaceutical Association.

Antonio Gómez-Muñoz et al. 5-Aminosalicylate stimulates phospholipase D activity in macrophages; Biochimica et Biophysica Acta; 2001; pp. 110-118; 1533; Elsevier Science B.V.

* cited by examiner

Scheme I

Scheme II

SYNTHESIS OF AZO BONDED IMMUNOREGULATORY COMPOUNDS

CROSS-REFERENCE TO RELATED APPLICATIONS

This application is a divisional application of U.S. patent application Ser. No. 13/094,135 filed on Apr. 26, 2011, now U.S. Pat. No. 8,314,214 which in turn was a divisional application of Ser. No. 11/631,582, filed on Jan. 4, 2007, now U.S. Pat. No. 7,932,366, which in turn was filed under the provisions of 35 U.S.C. §371 and claimed priority of International Patent Application No. PCT/US2005/024109, filed on Jul. 7, 2005, and which in turn claimed priority of U.S. Provisional Application No. 60/585,995 filed on Jul. 7, 2004.

BACKGROUND OF THE INVENTION

1. Field of the Invention

The present invention relates to immunoregulatory compounds, methods of producing same and methods of treating diseases therewith.

2. Background of the Invention

Many people suffer from inflammatory bowel disease (IBD). IBD is a generic term used to refer to two inflammatory diseases, ulcerative colitis and Crohn's disease, and various medications are being used to treat inflammatory bowel disease. For example, mesalamine, 5-aminosalicylic acid (5-ASA) is used to treat ulcerative colitis, but is associated with various side effects. It can be absorbed as it passes through the GI tract, which can adversely affect the amount of mesalamine that reaches the lower GI tract, particularly the colon and rectum. Sulfasalazine has also been used, but is metabolized in the body to form mesalamine (5-aminosalicylic acid (5-ASA)) and sulfapyridine. Accordingly, sulfasalazine is associated with several adverse side affects, including nausea, vomiting, abdominal discomfort, male infertility, and headache. These adverse side effects are usually attributed to the activity of sulfapyridine in the GI tract, as well as that absorbed into the system. Olsalazine has also been used to treat ulcerative colitis, but is both relatively expensive to make and associated with adverse side effects including diarrhea.

Efforts have been made to minimize the side effects associated with these compounds, including efforts by the present inventors to provide compounds that, when reaching the gut mucosa, break down into one or more active compounds useful for treating inflammatory bowel disorders. Examples of such compounds are described, for example, in U.S. Pat. No. 6,583,128 to Ekwuribe et al.

It would be beneficial to provide additional synthetic methods for preparing these compounds. The present invention provides such synthetic methods.

SUMMARY OF THE INVENTION

Synthetic methods for preparing compounds of the following formula are provided:

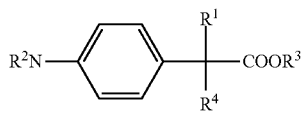

(I)

where $R^1$, $R^3$, and $R^4$ are independently hydrogen or $C_1$ to $C_4$ alkyl, and $R^2$ is:

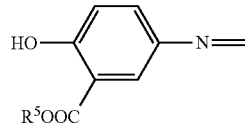

where $R^5$ is selected from the group consisting of hydrogen and $C_1$ to $C_4$ alkyl, or

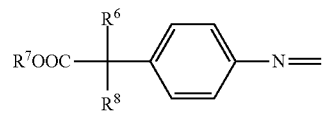

where $R^6$, $R^7$ and $R^8$ are independently hydrogen or $C_1$ to $C_4$ alkyl, as well as the esters or pharmaceutically acceptable salts of such compounds.

The compounds prepared by these methods can be included in pharmaceutical compositions, and used in methods of treating inflammatory conditions.

The active pharmaceutical ingredient may further comprise a compound of Formula III:

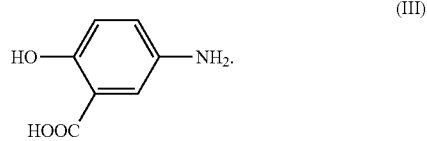 [SMILES: Nc1ccc(O)c(C(=O)O)c1]

(III)

The first step of the synthesis typically starts with an aniline compound, which is converted to a diazonium salt. In one embodiment, the aniline compound to be converted to the diazonium salt includes a primary alcohol or aldehyde group, which can be oxidized to a carboxylic acid group following formation of the diazonium salt and coupling to a desired molecule.

In another embodiment, the aniline compound to be converted to the diazonium salt includes a nitrile or amide group, which can be hydrolyzed to the carboxylic acid following formation of the diazonium salt and coupling to a desired molecule.

The second step of the synthesis involves forming a diazonium salt, which can be performed using known chemistry. The resulting diazonium salt is then coupled with a compound of the formula:

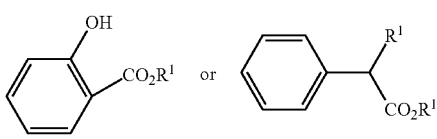

This coupling step typically provides predominantly a substitution at the 5-position of the salicylate, or a para substitution. In the embodiments where the aniline includes a primary alcohol or aldehyde group, the next step involves oxidizing the primary alcohol or aldehyde group to a carboxylic acid group. This can be accomplished using traditional oxidation chemistry, but optionally is performed using a catalytic amount of a chromium (VI) oxidant or other suitable oxidant in the presence of a stoichiometric amount of periodic acid.

In the embodiments where the aniline includes a nitrile or amide group, the next step involves hydrolysis of the amide or nitrile to the carboxylic acid. The hydrolysis can be either acid or base catalyzed. However, nitrilases and/or amidases can also be used, which typically results in milder reaction conditions.

In either embodiment, following the oxidation of the primary alcohol or aldehyde to the carboxylic acid, or hydrolysis of the amide or nitrile to the carboxylic acid, a pharmaceutically acceptable carboxylate salt or suitable ester (i.e., where $R^1$ on the $CO_2R^1$ group is alkyl) can be formed using routine chemistry.

In an alternative embodiment of the first approach (where the aniline to be converted to the diazonium salt includes a primary alcohol or aldehyde group, the methods first involve converting a compound of the formula:

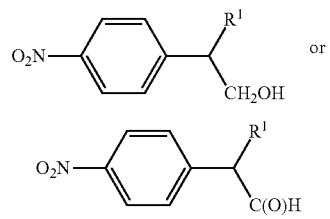

to a compound of formula:

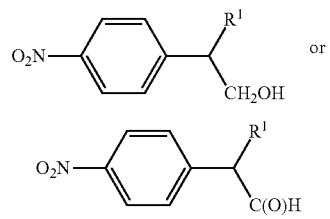

This conversion can be performed using standard reaction conditions well known to those of skill in the art, for example, as shown below with respect to the nitrobenzene including the primary alcohol group:

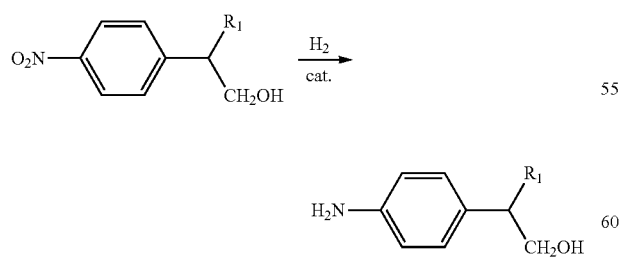

In an alternative embodiment of the second approach (where the aniline to be converted to the diazonium salt includes a nitrile or amide group), the methods first involve converting a compound of the formulas:

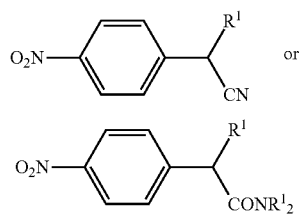

to a compound of the formulas:

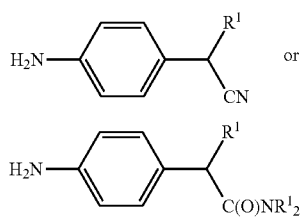

The amide group can optionally include one or two alkyl, aryl, arylalkyl or alkylaryl groups in place of one or both of the hydrogen atoms, which groups are removed when the amide is hydrolyzed to the carboxylic acid. However, since such groups would not be present in the final molecule, it is often easier to simply use an unsubstituted amide group (i.e., $CONH_2$).

This conversion can be performed using standard reaction conditions well known to those of skill in the art, for example, as shown below:

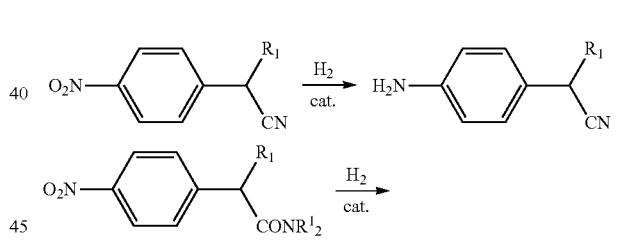

In still another embodiment, the starting materials for the reaction are nitrobenzene compounds such as:

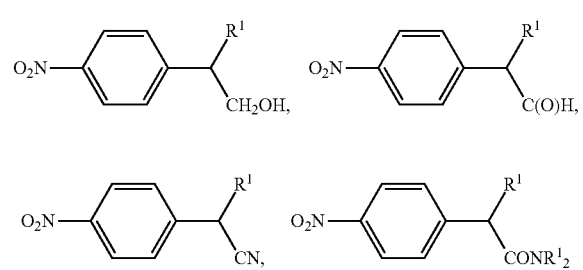

which are coupled with a compound of the formula:

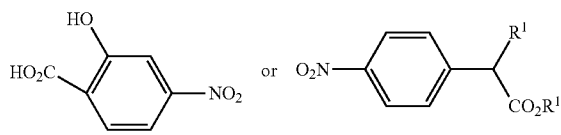

using a reagent such as lithium aluminum hydride ("LiAlH$_4$"), which is known in the art to couple nitrobenzenes to form azo compounds. Desired compounds are isolated and purified.

Alternatively, two compounds of the formula:

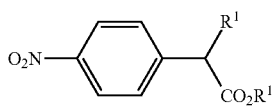

can be coupled directly, forming an azo linkage. Potential limitations to this approach are that when two different starting nitrobenzenes are used, three types of azo couplings are possible (A-A, A-B, B-B). Further, the reducing agent can reduce aldehyde, amide and nitrile groups, which then need to be reoxidized to form the carboxylic acid moieties. For this reason, it can be advantageous to perform the direct azo coupling of nitrobenzenes with starting materials that already include a carboxylic acid moiety (or carboxylate salt form thereof).

DETAILED DESCRIPTION OF THE INVENTION

The invention will now be described with respect to preferred embodiments described herein. It should be appreciated however that these embodiments are for the purpose of illustrating the invention, and are not to be construed as limiting the scope of the invention as defined by the claims.

As shown below, various synthetic methods are provided for preparing the compounds described herein.

Figure 1:
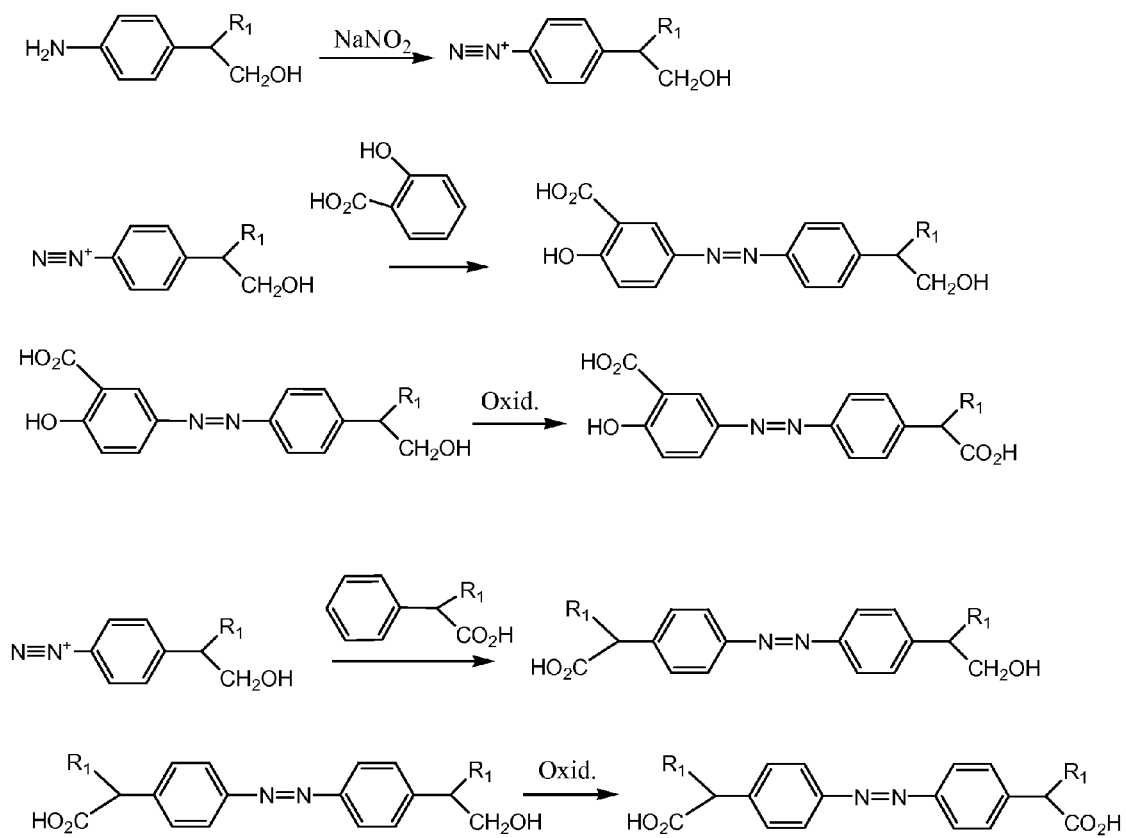
FIG. 1 illustrates embodiments of the synthesis routes described herein.

In a first embodiment (Scheme I in FIG. 1), an aniline derivative including a primary alcohol or aldehyde group is used, where the primary alcohol or aldehyde group is ultimately oxidized to form a carboxylic acid. The carboxylic acid group can optionally be converted to a pharmaceutically acceptable carboxylate salt or ester.

Figure 2:
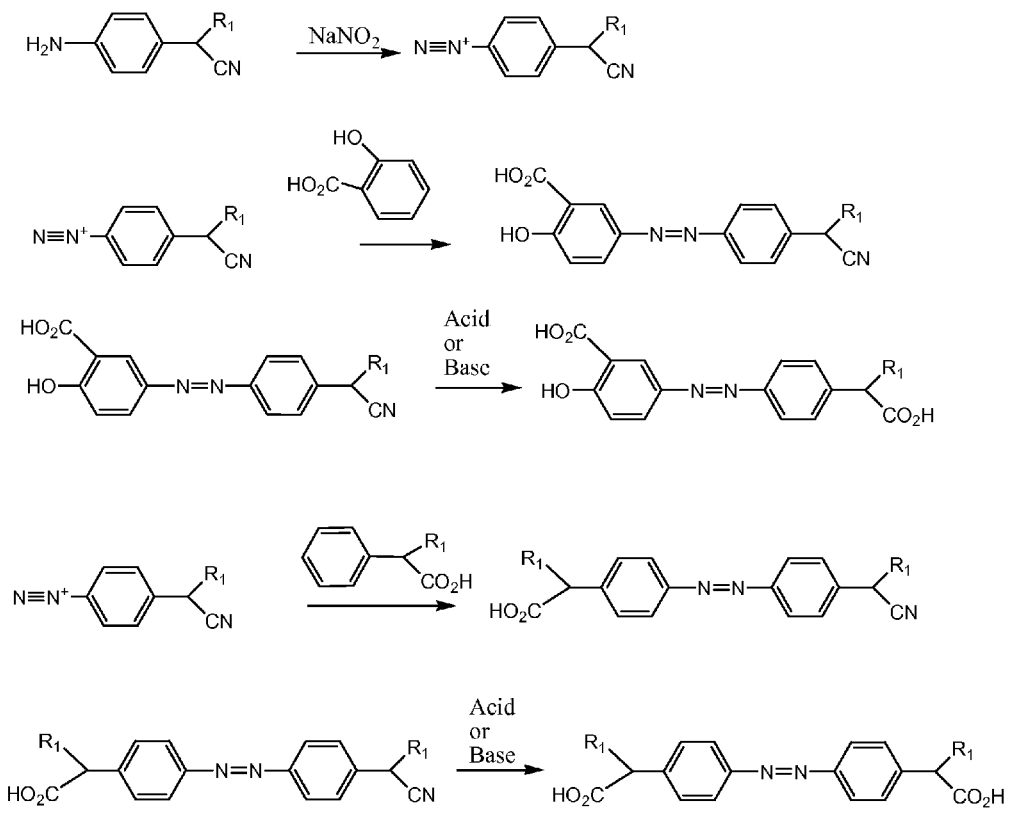
FIG. 2 illustrates additional embodiments of the synthesis routes described herein.

In a second embodiment (Scheme II in FIG. 2), an aniline derivative including a nitrile or amide group is used, where the nitrile or amide group is ultimately hydrolyzed to form a carboxylic acid. The first step in either embodiment involves forming a diazonium salt.

In a third embodiment, nitrobenzenes (rather than anilines) are used as starting materials, and are reduced to form the aniline starting materials used in the first two embodiments.

In a fourth embodiment, two nitrobenzenes are directly coupled to form an azo linkage, using a reducing agent such as lithium aluminum hydride.

Each of these reaction conditions and the associated starting materials will be better understood with reference to the following detailed description.

The Compounds

The compounds synthesized using the methods described herein include those having the following formula:

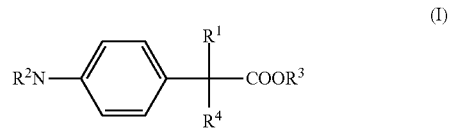

(I)

where $R^1$, $R^3$, and $R^4$ are independently hydrogen or $C_1$ to $C_4$ alkyl. Preferably, $R^1$, $R^3$, and $R^4$ are independently selected from the group consisting of H, $CH_3$, $CH_2CH_3$, and $CH(CH_3)_2$. More preferably, $R^1$, $R^3$, and $R^4$ are H or $CH_3$.

$R^2$ is:

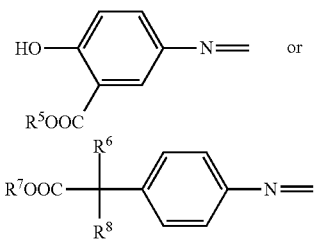

$R^5$ is selected from the group consisting of hydrogen and $C_1$ to $C_4$ alkyl. Preferably, $R^5$ is selected from the group consisting of H, $CH_3$, $CH_2CH_3$, and $CH(CH_3)_2$. More preferably, $R^5$ is H or $CH_3$ and, most preferably, $R^5$ is H. $R^6$, $R^7$ and $R^8$ are independently hydrogen or $C_1$ to $C_4$ alkyl. Preferably, $R^6$, $R^7$ and $R^8$ are independently selected from the group consisting of H, $CH_3$, $CH_2CH_3$, and $CH(CH_3)_2$. More preferably, $R^6$, $R^7$ and $R^8$ are independently H or $CH_3$.

Synthetic Methods

The individual reaction steps are discussed in more detail below.

Nitrobenzene Reduction to Aniline Starting Materials

In an alternative embodiment of the embodiment shown in Scheme 1 (where the aniline to be converted to the diazonium salt includes a primary alcohol or aldehyde group), the methods first involve converting a compound of the formula:

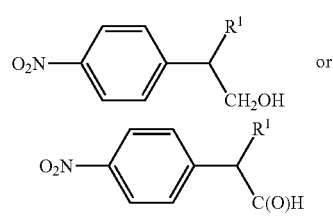

to a compound of formula:

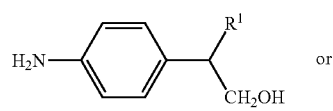

-continued

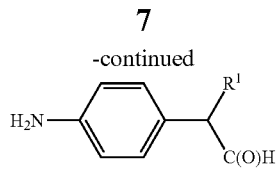

This conversion can be performed using standard reaction conditions well known to those of skill in the art, for example, as shown below:

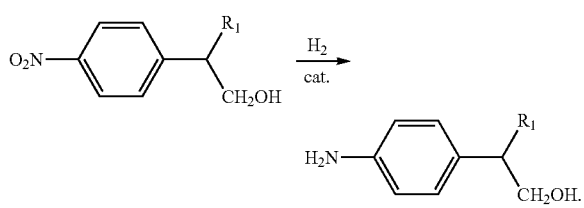

In an alternative embodiment of the embodiment in Scheme II (where the aniline to be converted to the diazonium salt includes a nitrile or amide group), the methods first involve converting a compound of the formulas:

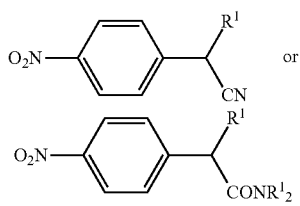

to a compound of the formulas:

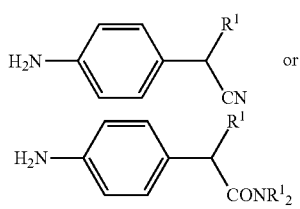

where $R^1$ is as defined above. The amide group can include one or two alkyl, aryl, arylalkyl or alkylaryl groups (in addition to those defined by $R^1$) such as are well known in the art in place of one or both of the hydrogen atoms, which groups are removed when the amide is hydrolyzed to the carboxylic acid. However, since such groups would not be present in the final molecule, it is often easier to simply use an unsubstituted amide group (i.e., $CONH_2$).

This conversion can be performed using standard reaction conditions well known to those of skill in the art, for example, as shown below:

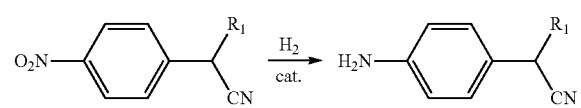

-continued

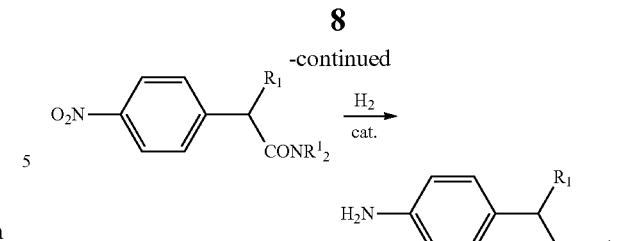

Conversion of Anilines to Diazonium Salts

The first step in Scheme I involves converting an aniline compound to a diazonium salt. The aniline compounds include a primary alcohol or aldehyde group, and the conversion involves the known reaction with $NaNO_2$ to convert anilines to diazonium salts. Such reaction conditions are well known to those of skill in the art, and the reactions are shown below.

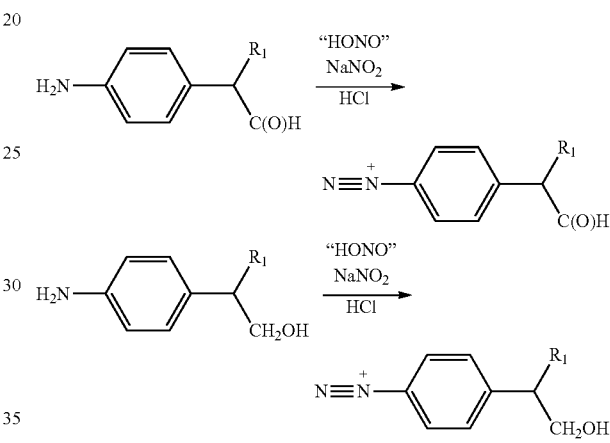

The first step in Scheme II also involves converting an aniline compound to a diazonium salt. The aniline compounds include a nitrile or amide group, and the conversion similarly involves the known reaction with $NaNO_2$ to convert anilines to diazonium salts. The reactions are shown below.

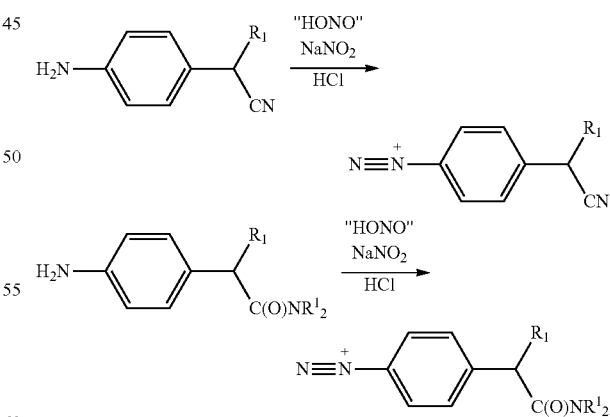

In the reactions shown above, $R^1$ is as defined elsewhere in this application. It is also contemplated that with respect to the amide groups, any substitution on the amide linkage that does not interfere with the subsequent chemistry is acceptable, since the amide is later hydrolyzed to the carboxylic acid and such groups will not appear, in any case, in the final molecule. Such groups include, for example, $C_{1-10}$ straight, branched or cyclic alkyl groups, aryl groups such as those including one or more benzene or naphthalene rings, alkyl groups substituted with aryl groups (alkylaryl groups), aryl groups substituted with one to five alkyl groups (arylalkyl groups) and the like.

Electrophilic Aromatic Substitution Using Diazonium Salts

Electrophilic aromatic substitution reactions using diazonium salts are well known. The following two aromatic compounds are substituted with the previously described diazonium salts:

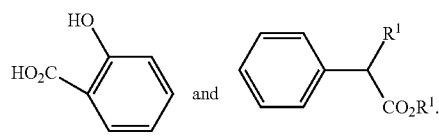

With respect to the first compound, substitution primarily takes place at a position para to the phenol group and meta to the carboxylic acid group. With respect to the second compound, substitution primarily takes place at a position para to the substituted (with $R^1$) acetic acid group. The following reactions take place in connection with Scheme I.

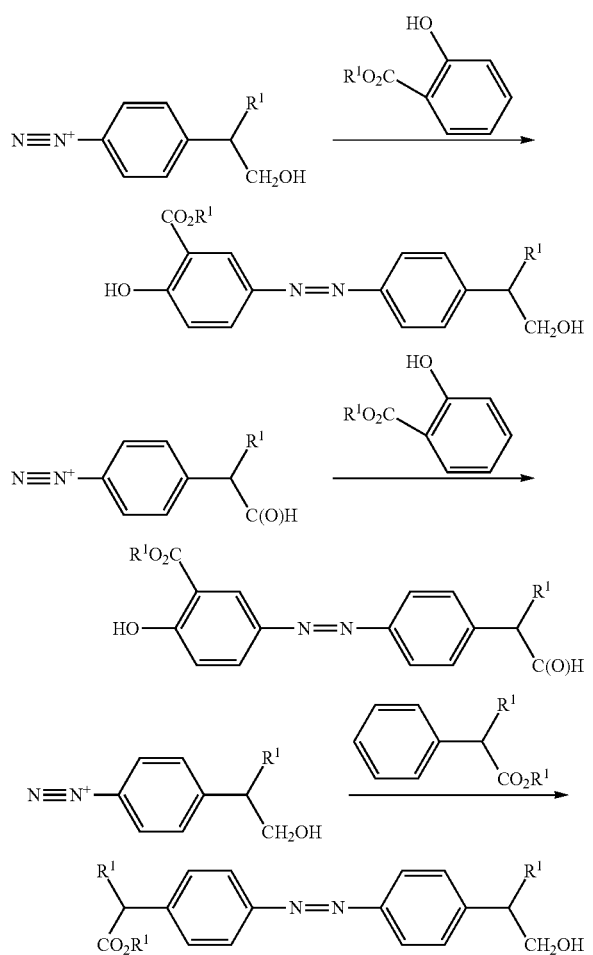

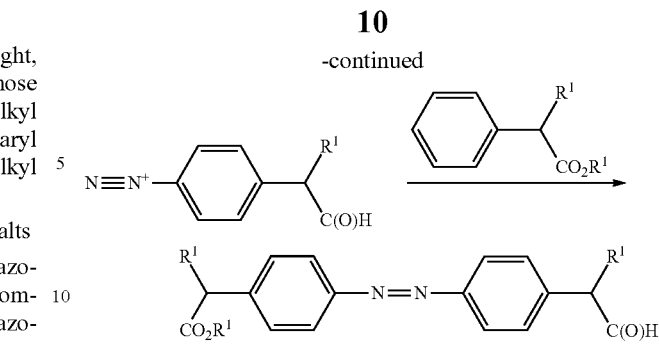

The following reactions take place with respect to Scheme II:

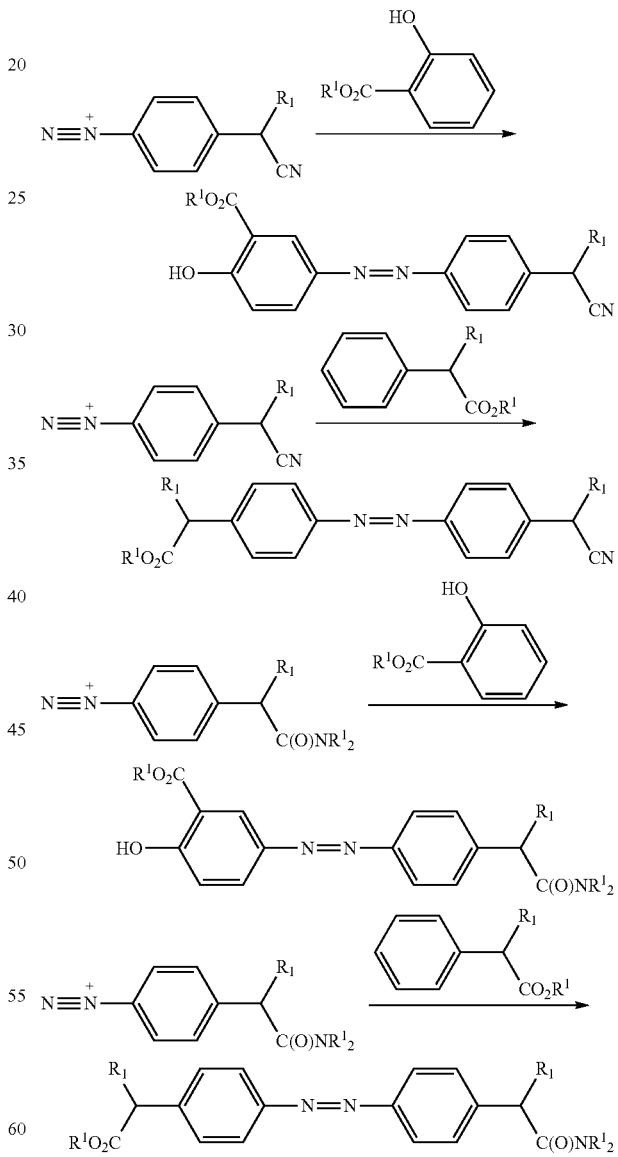

Oxidation of Primary Alcohol and Aldehyde Groups

With respect to Scheme I, the primary alcohol or aldehyde groups in the intermediate resulting from the diazonium coupling reaction are then oxidized to carboxylic acid groups.

The reactions are shown below:

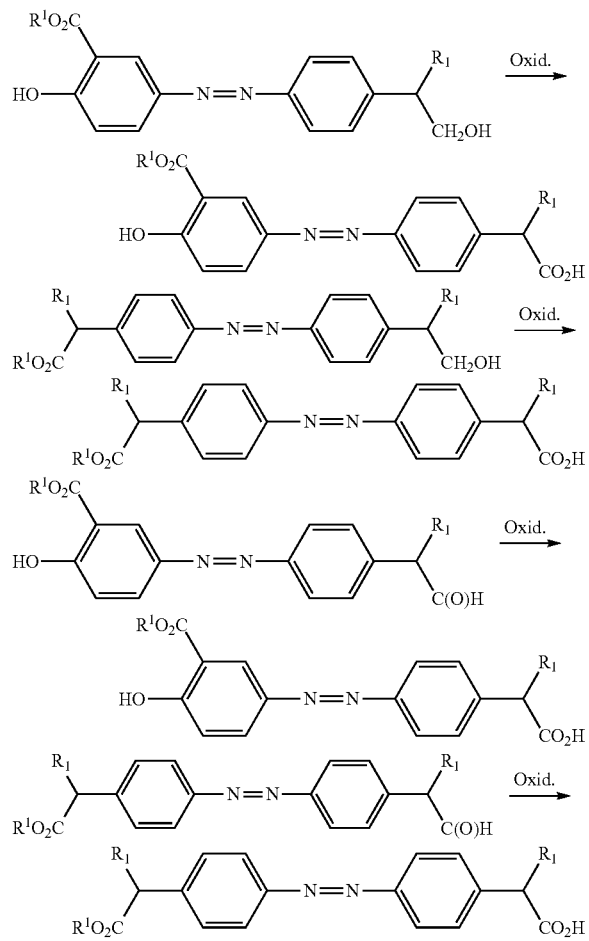

In some embodiments, particularly those embodiments where there is a phenol group present, the oxidation chemistry may oxidize the phenol to a quinone-type compound. In such embodiments, the phenol can be protected with conventional protecting group chemistry (e.g., as a silyl ether, a THP ether, a benzyloxy, an ester, and the like), and deprotected after the oxidation step. Examples of suitable protecting groups for phenol groups which are amenable to various oxidation conditions are well known to those of skill in the art ((see Greene, T. W.; Wuts, P. G. M. Protective Groups in Organic Synthesis, 2nd ed.; Wiley: New York, 1991, the contents of which are hereby incorporated by reference).

U.S. Pat. No. 6,150,554 to Li et al., the contents of which are hereby incorporated by reference, teaches the oxidation of primary alcohols to carboxylic acids using catalytic $CrO_3$ and periodic acid (referred to in the literature as both $HIO_4$ and $H_5IO_6$) as the stoichiometric oxidant. This chromium catalyzed oxidation method avoids the chromium disposal issues associated with running a typical Jones oxidation reaction with stoichiometric $CrO_3$, reduces the epimerization of any α-chiral centers, and is a one step procedure. The reaction is mild, rapid, high yielding and only requires 1-2 mol % of $CrO_3$.

The oxidation of primary alcohols to carboxylic acids is well known in the art of organic synthesis. Typical reagents include chromium (VI) oxidizing agents (including, but not limited to, sodium and potassium dichromate, chromic acid, and the like), and manganese (VII) oxidizing agents such as potassium permanganate. The oxidation of aldehydes to carboxylic acids is also well known. While the same strong oxidizing agents used to oxidize primary alcohols can be used, much milder oxidizing agents can also be used. For example, ozone (or oxygen) and ultraviolet light and/or a suitable catalyst can often be used. Representative reaction conditions are described, for example, in U.S. Pat. No. 6,680,395 to Springer, the contents of which are hereby incorporated by reference.

Industrially, it is often preferred to use the mildest and/or least expensive oxidation conditions that result in the desired products. Accordingly, it can be preferred to use oxygen or ozone as an oxidizing agent where appropriate, or to use catalytic chromium (VI) salts along with a co-oxidizing agent such as periodic acid to regenerate the catalytic chromium (VI) salts where appropriate.

Hydrolysis of Nitrile and Amide Groups

The embodiment in Scheme II does not require the use of primary alcohols in the starting material, so that oxidation from a primary alcohol to a carboxylic acid group can be avoided. This embodiment involves the use of an aniline that includes a nitrile (—CN) or amide (—C(O)$NR^1_2$) group in place of the primary alcohol group. The nitrile or amide groups can be hydrolyzed to a carboxylic acid group after the diazonium salt is coupled to a desired aromatic ring. The reactions are shown below.

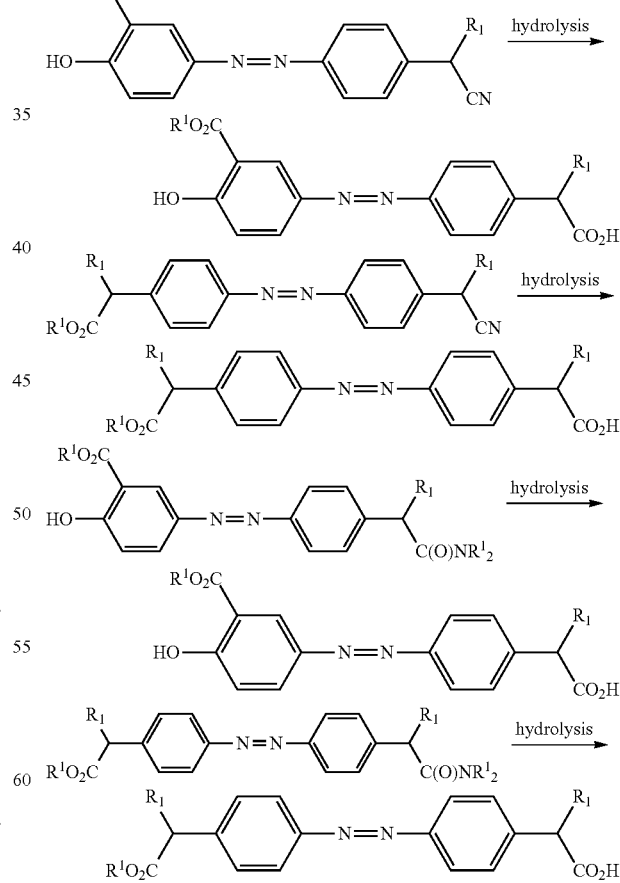

Reaction conditions for converting a nitrile to a carboxylic acid group are well known to those of skill in the art, and are described, for example, in March, J. Advanced Organic Chemistry; 3rd ed., John Wiley: New York, (1985) and House, Modern Synthetic Reactions, 2d. ed., W.A. Benjamin, Inc., Menlo Park, Calif., (1972). The conditions involve either using an acid or a base to catalyze the hydrolysis. A tautomer of an amide is believed to be an intermediate in the hydrolysis of a nitrile group to a carboxylic acid. For this reason, an amide group can be used in place of the nitrile for purposes of carrying out the synthetic method.

Biocatalytic hydrolysis of nitriles to carboxylic acids can be carried out under mild conditions, without affecting other functional groups. The nitrile group thus functions as a "masked" acid group. Nitrilase enzymes (for example, those from *Arabidopsis thaliana, Alcaligenes faecalis, Pseudomonas fluorescens, Rhodococcus rhodochrous*, and *Rhodococcus* sp.) are available commercially from companies such as Sigma-Adrich. The chemistry is described, for example, in Effenger and Osswald, "Catalyst for the (E)-selective hydrolysis of (E,Z)-α,β-unsaturated nitriles to carboxylic acids," *Tetrahedron: Asymmetry*, 12:2581 (2001); Effenger and Osswald, "Selective hydrolysis of aliphatic dinitriles to monocarboxylic acids, *Synthesis*, 1866 (2001); and Effenger and Osswald, "Enantioselective hydrolysis of (1)-arylacetonitriles, *Tetrahedron: Asymmetry*, 12:279 (2001), the contents of which are hereby incorporated by reference. Because the biocatalytic hydrolysis can involve milder conditions than either the acid or basic hydrolysis of nitriles, this method can be preferred, particularly for industrial synthesis of the compounds described herein.

A large number of amidases (enzymes that cleave amide groups) are also known and can be used to hydrolyze the amides to carboxylic acids. One potential advantage of using the amidases is that they tend to be selective for one enantiomer over another. In some embodiments, the compounds are formed as racemic mixtures or mixtures of diastereomers, and the amidases allow (via enzymatic resolution) the individual enantiomers or diastereomers to be separated. Of course, conventional methods, such as selective crystallization, chiral chromatography and the like, as are well known to those of skill in the art, can also be used to isolate enantiomerically enriched compounds.

The resulting carboxylic acid-containing compounds can often be easily separated from the amide-containing compounds by simply forming the carboxylate salts, which can be removed in a water extraction and then isolated by acidification of the carboxylate group to reform the carboxylic acid group. The amide groups not hydrolyzed by the enzyme (or, for that matter, via conventional acidic or basic hydrolysis) can be isolated from extraction with an organic solvent, and subjected to alternate hydrolysis conditions.

Optionally, the carboxylic acid groups can be converted to pharmaceutically acceptable carboxylate salts or esters, using known reaction conditions.

Direct Azo Coupling of Nitrobenzenes Using Reducing Agents

Nitrobenzene starting materials can be directly coupled to form azo linkages using a reducing agent such as lithium aluminum hydride. Representative reactions using the nitrobenzene compounds are shown below:

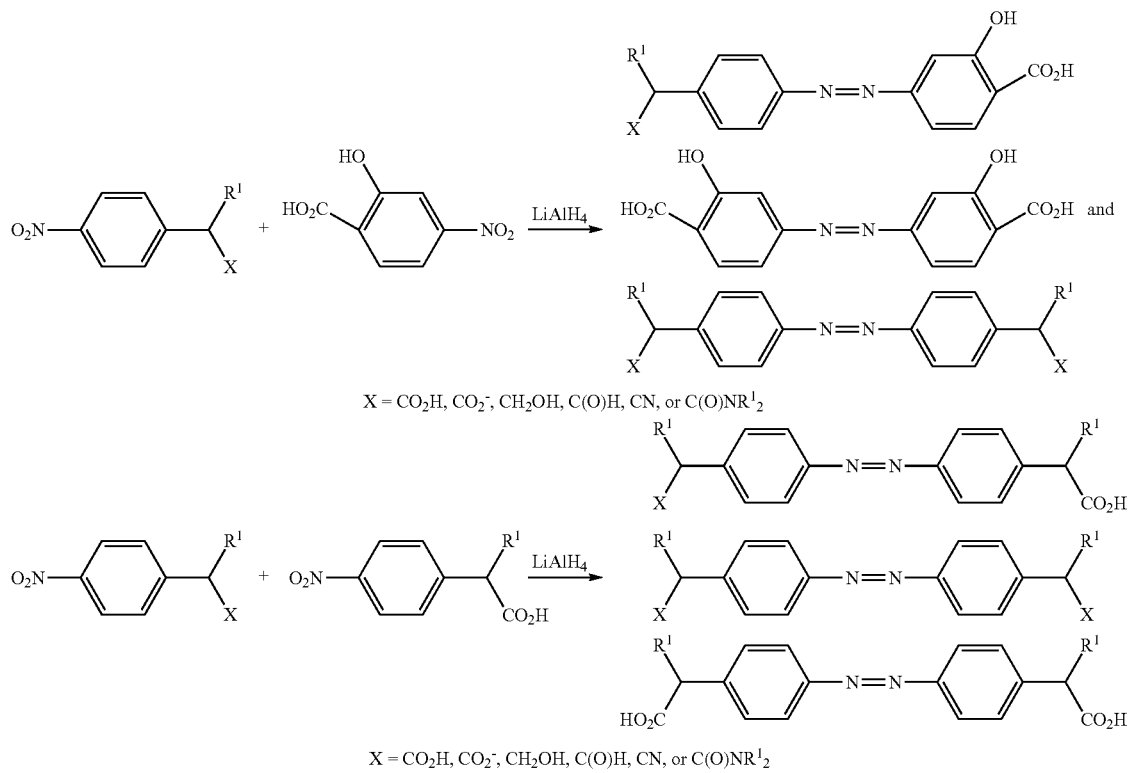

X = CO$_2$H, CO$_2^-$, CH$_2$OH, C(O)H, CN, or C(O)NR$^1{}_2$

X = CO$_2$H, CO$_2^-$, CH$_2$OH, C(O)H, CN, or C(O)NR$^1{}_2$

In the first instance, the three different azo coupling products will likely have to be separated. In the second instance, the compounds are either identical (X is CO$_2$H or CO$_2^-$), or X is readily convertible to a carboxylic acid group, so that separation need not be performed. That is, if X is an aldehyde or primary alcohol, it can be oxidized in the presence of the carboxylic acid group to yield the desired compound. If X is a nitrile or amide group, it can be hydrolyzed in the presence of the carboxylic acid group to yield the desired compound. For these reasons, it may be advantageous to use this embodiment (azo coupling of nitrobenzenes) only when the molecules are either symmetrical or would be symmetrical when X is converted to a carboxylic acid group. It is also worth noting that aldehyde, amide and nitrile groups can be reduced with the reducing agent (for example, lithium aluminum hydride). The stoichiometric equivalents of the reducing agent may need to be adjusted to account for this, and any reduced groups will need to be oxidized to form the carboxylic acid. For this reason, it may be preferred to use compounds where X is a carboxylic acid or carboxylate group when performing this reaction. Finally, any suitable carboxylate salt can be used (that is, any metal cation or ammonium cation can be used) if the desired end product includes a carboxylic acid at that position, as the acidification of virtually any carboxylate salt to form the carboxylic acid is routine in the art. That is to say, for cost reasons, it may be preferred to use a sodium or potassium salt, although other salts would certainly be acceptable.

Pharmaceutical Formulations

The compounds prepared according to the methods described herein can be included in pharmaceutical formulations, both for veterinary and for human medical use. The compounds can be administered per se as well as in the form of pharmaceutically acceptable esters, salts, and other physiologically functional derivatives thereof.

The formulations include those suitable for parenteral as well as non-parenteral administration, and specific administration modalities include, but are not limited to, oral, rectal, buccal, topical, nasal, ophthalmic, subcutaneous, intramuscular, intravenous, transdermal, intrathecal, intra-articular, intra-arterial, sub-arachnoid, bronchial, lymphatic, vaginal, and intra-uterine administration. Formulations suitable for oral and parenteral administration are preferred, with formulations suitable for oral administration most preferred.

In addition to the aforementioned ingredients, the formulations of this invention can further include one or more accessory ingredient(s) selected from diluents, buffers, flavoring agents, disintegrants, surface active agents, thickeners, lubricants, preservatives (including antioxidants), and the like.

The active pharmaceutical ingredient can further include one or more other medicaments including, but not limited to, anti-inflammatory agents such as mesalamine, sulfasalazine, balsalazide, and olsalazine; immunomodulators such as azathioprine, 6-mercaptopurine, cyclosporine and methotrexate; steroidal compounds such as corticosteroids; and antibiotics such as metronidazole and ciprofloxacin. The active pharmaceutical ingredient preferably further comprises mesalamine, the compound of Formula II:

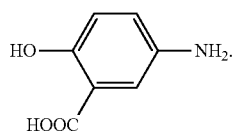

(II)

In therapeutic usage, the compounds can be used to treat an animal subject having or latently susceptible to an intestinal condition(s) or disease state(s) and in need of treatment therefor, by administering an effective amount of the compound to the animal. The animal can be a human or non-human animal (e.g., bird, dog, cat, cow, horse), preferably a mammal, and most preferably a human.

The compounds can be used to treat and/or prevent various diseases, particularly inflammatory conditions of the GI tract including, but not limited to, inflammatory conditions of the mouth such as mucositis, infectious diseases (e.g., viral, bacterial, and fungal diseases), and Crohn's disease; inflammatory conditions of the esophagus such as esophagitis, conditions resulting from chemical injury (e.g., lye ingestion), gastroesophageal reflux disease, bile acid reflux, Barrett's esophagus, Crohn's disease, and esophageal stricture; inflammatory conditions of the stomach such as gastritis (e.g., *Helicobacter pylori*, acid-peptic disease and atrophic gastritis), peptic ulcer disease, pre-cancerous lesions of the stomach, non-ulcer dyspepsia, and Crohn's disease; inflammatory conditions of the intestine such as inflammatory bowel disease, celiac disease, Crohn's disease, bacterial overgrowth, peptic ulcer disease, and fissures of the intestine; inflammatory conditions of the colon such as Crohn's disease, ulcerative colitis, infectious colitis (e.g., pseudomembranous colitis such as *Clostridium difficile* colitis, salmonella enteritis, shigella infections, yersiniosis, cryptosporidiosis, microsporidial infections, and viral infections), radiation-induced colitis, colitis in the immunocompromised host (e.g., typhlitis), precancerous conditions of the colon (e.g., dysplasia, inflammatory conditions of the bowel, and colonic polyps), proctitis, inflammation associated with hemorrhoids, proctalgia fugax, and rectal fissures; liver gallbladder and/or biliary tract conditions such as cholangitis, sclerosing cholangitis, primary biliary cirrhosis, and cholecystitis; and intestinal abscess. The compounds can also be used to diagnose constituents, conditions, or disease states in biological systems or specimens, as well as for diagnostic purposes in non-physiological systems. Furthermore, the compounds can be used to treat or prevent condition(s) or disease state(s) in plant systems. By way of example, the compounds or individual active components of the conjugate can have insecticidal, herbicidal, fungicidal, and/or pesticidal efficacy amenable to usage in various plant systems.

Depending on the specific condition or disease state, the active pharmaceutical ingredient can be administered at any suitable therapeutically effective and safe dosage, as can readily be determined within the skill of the art and without undue experimentation. For example, the active pharmaceutical ingredient of the present invention can be administered at a dosage between about 0.1 and 200 mg/kg, preferably between about 1 and 90 mg/kg, and more preferably between about 10 and 80 mg/kg.

In some embodiments, the compounds can break down in the intestinal tract to form the metabolic product of Formula III:

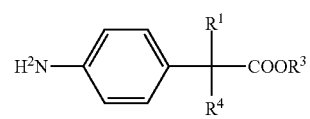

(III)

where $R^1$, $R^3$ and $R^4$ are as described above with reference to Formula I, and the metabolic product of Formula IV:

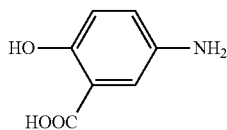

(IV)

The metabolic product of Formula III can possess anti-inflammatory activity and/or immunoregulatory activity. The metabolic product of Formula IV can possess anti-inflammatory activity, and more particularly can inhibit prostaglandin synthetase I & II.

In other embodiments, the compounds can break down in the intestinal tract to form the metabolic product of Formula III and the metabolic product of Formula V:

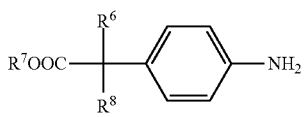

(V)

where $R^6$, $R^7$ and $R^8$ are as described above with reference to Formula I. The metabolic product of Formula V can possess anti-inflammatory activity and/or immunoregulatory activity. Accordingly, the compounds can provide immunoregulatory activity. The compounds can also inhibit prostaglandin synthetase I and II. The compounds can be used to treat various diseases, particularly ulcerative colitis, Crohn's disease and the like.

The present invention will now be described with reference to the following examples. It should be appreciated that these examples are for the purposes of illustrating aspects of the present invention, and do not limit the scope of the invention as defined by the claims.

EXAMPLES

Example 1

Diazo Coupling of 4-Aminophenethyl Alcohol with Salicylic Acid, Followed by Oxidation of the Alcohol to the Corresponding Carboxylic Acid Diazo Coupling of 4-Aminophenethyl Alcohol with Salicylic Acid:

4-Aminophenethyl alcohol (24.8 mmol) is suspended in water (75 mL) and concentrated hydrochloric acid (8 mL) is added. The solution is cooled to 0° C. in an ice bath with rapid stirring. Sodium nitrite (26.1 mmol) in water (20 mL) is added dropwise to the 4-aminophenylacetic acid solution with rapid stirring. It may be important to keep the temperature between 0-5° C. at all times, especially during the $NaNO_2$ addition. The reaction is stirred for an additional period of time, for example, about 20 minutes. In the meantime, salicylic acid, sodium salt (74.4 mmol) is dissolved in an aqueous NaOH solution (113 mmol NaOH in 100 mL $H_2O$). The solution is vigorously stirred at 17° C. and at pH 13.3. The diazonium salt solution is added dropwise to the salicylic acid solution. It can be important to keep the temperature of the salicylic acid solution between 17-18° C. and the pH between 13.2-13.3 at all times, especially during the diazonium salt addition. The temperature can be regulated by adding ice and the pH regulated by adding NaOH, for example, 8M NaOH. After the addition is complete, the solution is allowed to warm room temperature and stirred for an additional period of time, for example, about 30 minutes. The reaction mixture is then suction filtered to remove any undissolved particulates or unwanted side products. The filtrate is acidified with aqueous HCl (10 mL conc. HCl in 20 mL $H_2O$) which produces a dark red precipitate. The precipitate is collected by suction filtration and washed several times with cold $H_2O$, until the filtrate is clear. The collected solid can be air dried overnight.

Oxidation of the Resulting Alcohol to the Corresponding Carboxylic Acid:

A mixture of alcohol formed above (0.7 mol) and a solution of sodium carbonate is placed in 150 mL of water. A solution of potassium permanganate (0.9 mol) in water is added, with vigorous stirring, for 3-4 hours at a temperature of 4-5° C. The reaction mixture is allowed to warm to room temperature and the precipitated manganese dioxide is removed by suction filtration. The solution is concentrated under reduced pressure, a layer of ether is added, and the aqueous solution is acidified with dilute $H_2SO_4$. The organic and aqueous phases are separated and the aqueous phase extracted 2-3 times with ether. The ether extracts are combined, dried over $MgSO_4$, and the solvent removed under reduced pressure. The resulting solid can optionally be recrystallized.

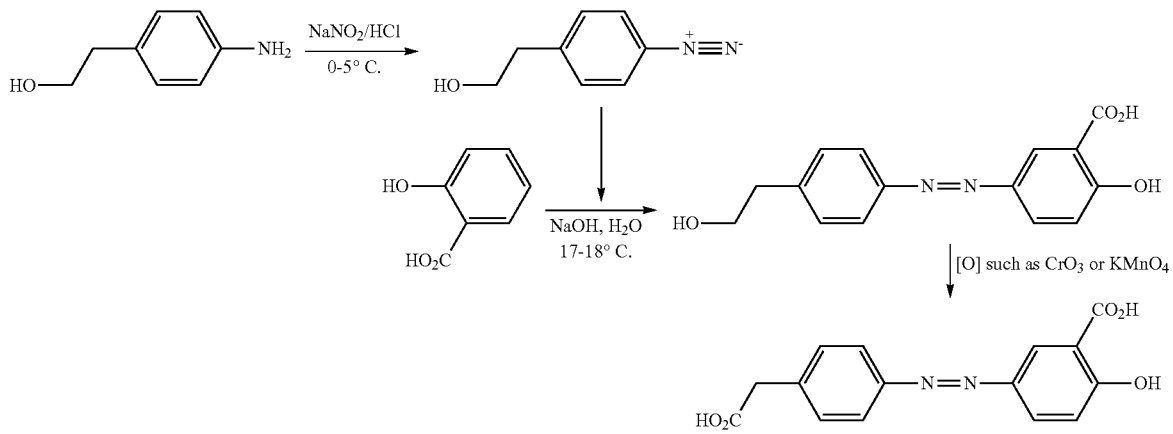

Example 2

Diazo Coupling of 4-Aminobenzyl Cyanide with Salicylic Acid, Followed by Hydrolysis of the Nitrile to the Corresponding Carboxylic Acid

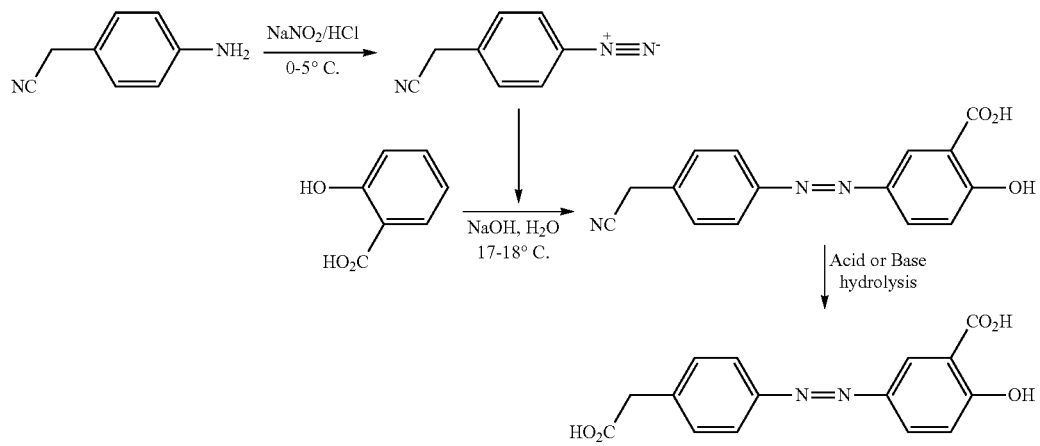

Diazo Coupling of 4-Aminobenzyl Cyanide with Salicylic Acid

4-Aminobenzyl cyanide (24.8 mmol) is suspended in water (75 mL) and concentrated hydrochloric acid (8 mL) is added. The solution is cooled to 0° C. in an ice bath with rapid stirring. Sodium nitrite (26.1 mmol) in water (20 mL) is added dropwise to the 4-aminophenylacetic acid solution with rapid stirring. It is preferred to keep the temperature between 0-5° C. at all times, especially during the $NaNO_2$ addition. The reaction is stirred for an additional 20 minutes. In the meantime, salicylic acid, sodium salt (74.4 mmol) is dissolved in an aqueous NaOH solution (113 mmol NaOH in 100 mL $H_2O$). The solution is vigorously stirred at 17° C. and at pH 13.3. The diazonium salt solution is added dropwise to the salicylic acid solution. It can be extremely important to keep the temperature of the salicylic acid solution between 17-18° C. and the pH between 13.2-13.3 at all times, especially during the diazonium salt addition. The temperature is regulated by adding ice and the pH regulated by adding NaOH, for example, 8M NaOH. After the addition is complete, the solution is allowed to warm room temperature and stirred for an additional period of time, such as about 30 minutes. The reaction mixture can be suction filtered to remove any undissolved particulates or unwanted side products, and the filtrate can be acidified with aqueous HCl (10 mL conc. HCl in 20 mL $H_2O$) to produce a dark red precipitate. The precipitate can be collected by suction filtration and washed several times with cold $H_2O$, until the filtrate is clear. The collected solid can be air dried overnight.

Hydrolysis of the Nitrile to the Corresponding Carboxylic Acid a) Basic Conditions:

The nitrile formed above (1.2 mol) and a solution of NaOH (2.3 mol) can be placed in $H_2O$ (260 mL) in a round-bottom flask and heat to reflux using a condenser for approximately 5-10 h. Water (100 mL) can be added through the condenser, then slowly with external cooling, 50% $H_2SO_4$ can be added. The upper layer containing the desired carboxylic acid can be separated and extracted with $CH_2Cl_2$. The organic extracts can be combined, dried over $MgSO_4$, and the solvent removed under reduced pressure. The resulting solid can optionally be recrystallized.

b) Acidic Conditions:

The nitrile formed above (0.85 mol) and a solution of 50:50 $H_2SO_4$:glacial acetic acid can be placed in $H_2O$ (100 mL) in a round-bottom flask and heated to reflux using a condenser for approximately 1 hour. The reaction mixture can be allowed to cool to room temperature and poured into 2-3 volumes of water with stirring. The desired crude product should precipitate. The resulting solid can be collected by suction filtration and washed with water until the filtrate is neutral. The resulting solid can optionally be recrystallized.

Example 3

Reduction of Nitro Compounds to Form an Azo Linkage

In this embodiment, two nitrobenzene compounds (shown below as $ArNO_2$) are coupled to form a direct azo linkage between the two compounds. This embodiment will result in mixtures of products (A-A, A-B and B-B) if two different nitrobenzene compounds are used. For this reason, it may be preferably to limit this synthetic approach to the synthesis of symmetrical azo compounds, e.g. 4-APAA dimer, etc. (Ar=Phenyl ring)

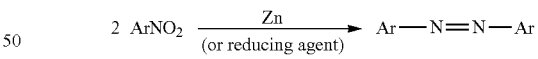

A solution of NaOH (1.6 mol) in $H_2O$ (150 mL), nitrobenzene (0.41 mol) and MeOH (500 mL) is placed in a 3-neck flask equipped with an overhead stirrer and reflux condenser. Zn powder (0.9 mol) is added and refluxed with vigorous stirring for approximately 10 h. The reaction mixture is hot filtered and the precipitate washed with MeOH. Concentrated HCl is added to the filtrate until the pH is neutral by litmus paper, and the precipitated is re-filtered. The MeOH is removed under reduced pressure and the resulting aqueous solution is cooled in an ice bath until the desired azo compound precipitates. The solid can then be collected by suction filtration and optionally recrystallized.

The foregoing is illustrative of the present invention, and is not to be construed as limiting thereof. The invention is defined by the following claims, with equivalents of the claims to be included therein.

That which is claimed is:

1. A method for preparing a compound of the formula:

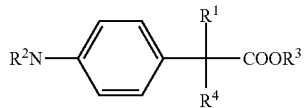
(I)

where $R^1$, and $R^3$ are selected from the group consisting of H, $CH_3$, $CH_2CH_3$, and $CH(CH_3)_2$;
$R^4$ is H and $R^2$ is:

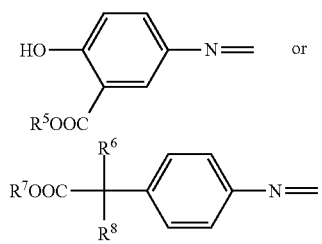

where $R^5$, $R^6$, $R^7$ and $R^8$ are independently hydrogen or $C_1$ to $C_4$ alkyl; or the esters or pharmaceutically acceptable salts thereof, comprising:

converting a compound of one of the following formulas:

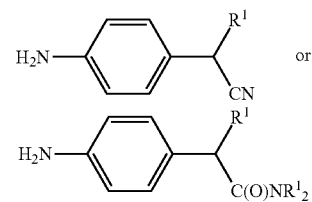

to a diazonium salt;
reacting the diazonium salt with a compound of one of the following formulas:

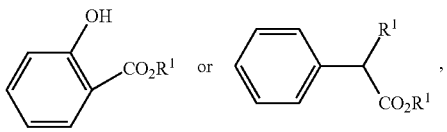

hydrolyzing the nitrile or amide group to form a carboxylic acid group, and optionally forming an ester or pharmaceutically acceptable salt of one or more of the carboxylic acid groups.

2. The method of claim 1, wherein the aniline starting material is formed by reducing a nitrobenzene of one of the following formulas:

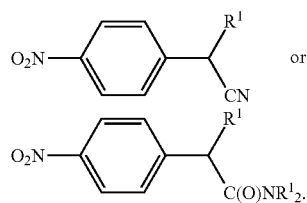

3. The method of claim 1, wherein the nitrile or amide is hydrolyzed to the carboxylic acid using acid catalysis.

4. The method of claim 1, wherein the nitrile or amide is hydrolyzed to the carboxylic acid using basic catalysis.

5. The method of claim 1, wherein the nitrile or amide is hydrolyzed to the carboxylic acid using enzymatic catalysis.

6. The method of claim 1, wherein $R^6$, $R^7$, and $R^8$ are independently selected from the group consisting of H, $CH_3$, $CH_2CH_3$, and $CH(CH_3)_2$.

7. The method of claim 1, wherein $R^5$ is selected from the group consisting of H, $CH_3$, $CH_2CH_3$, and $CH(CH_3)_2$.

8. The method of claim 1, wherein the compound that is formed is 5-(4-carboxymethyl-phenylazo)-2-hydroxy-benzoic acid, 5-[4-(1-carboxy-ethyl)-phenylazo]-2-hydroxy-benzoic acid or 4-(4-carboxymethyl-phenylazo)-phenylacetic acid.

* * * * *